US00PP15887P2

(12) United States Plant Patent
Olesen et al.

(10) Patent No.: US PP15,887 P2
(45) Date of Patent: Jul. 19, 2005

(54) ROSE PLANT NAMED 'POULEN009'

(50) Latin Name: *Rosa hybrida*
Varietal Denomination: POULen009

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 126 days.

(21) Appl. No.: 10/742,402

(22) Filed: Dec. 22, 2003

(51) Int. Cl.[7] ..... A01H 5/00
(52) U.S. Cl. ..... Plt./137
(58) Field of Search ..... Plt./137, 130, 141, Plt./148

*Primary Examiner*—Anne Marie Grunberg
*Assistant Examiner*—June Hwu

(57) ABSTRACT

A new garden rose plant of the hybrid tea class which has abundant, pink flowers and attractive foliage. This new and distinct variety has shown to be uniform and stable in the resulting generations from asexual propagation.

2 Drawing Sheets

Botanical classification: *Rosa hybrida.*
Variety denomination: 'POULen009'.

SUMMARY OF THE INVENTION

The present invention constitutes a new and distinct variety of garden rose plant which originated from a controlled crossing between an unnamed female parent plant and the male parent plant 'POULsyng', described and illustrated in U.S. Plant patent application Ser. No. 09/268,299 dated Mar. 16, 1999, now abandoned. The two parents were crossed during the summer of 1995 and the resulting seeds were planted in a controlled environment in Fredensborg, Denmark. The new variety is named 'POULen009'.

The new variety may be distinguished from its female parent, by the following combination of characteristics:

1. While the seed parent has a light pink flower bud. 'POULen009' has an orange flower bud.
2. The unnamed seed parent has small flowers of 5 to 8 cm. The same of 'POULen009' are 10 to 15 cm.

The new variety may be distinguished from its male pollen parent, 'POULsyng', by the following combination of characteristics:

1. While the pollen parent 'POULsyng' has a flower bud color of Orange Group 27B. The same of 'POULen009' is Yellow-Orange Group 19B.
2. Flowers of 'POULsyng' have 34 to 40 petals. 'POULen009' has 45 petals on average.

The objective of the hybridization of this rose variety was to create a new and distinct variety for garden use with unique qualities, such as:

1. Uniform and abundant pink flowers;
2. Vigorous, but compact growth when propagated both as a budded rose and on its own roots;
3. Disease resistance;
4. Exceptional fragrance.

This combination of qualities is not present in previously available commercial cultivars of this type, known to the inventors, and distinguish 'POULen009' from all other varieties of which we are aware.

As part of their rose development program, L. Pernille Olesen and Mogens N. Olesen germinated the seeds from the aforementioned hybridization during winter of 1995 and conducted evaluations on the resulting seedlings in a controlled environment in Fredensborg, Denmark.

'POULen009' was selected in the spring 1996 by the inventors as a single plant from the progeny of the aforementioned hybridization.

Asexual reproduction of 'POULen009' by traditional budding and rooted cuttings was first done by L. Pernille and Mogens N. Olesen in their nursery in Fredensborg, Denmark in July, 1996. This initial and other subsequent asexual propagations conducted in controlled environments have demonstrated that the characteristics of 'POULen009' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'POULen009'.

Specifically illustrated in SHEET 1:

FIG. 1.1; Open flower, stem showing cluster of open flowers, branching, and the attachment of leaves, buds, and peduncles;

FIG. 1.2; Flower bud closed, flower bud as sepals unfold, and partially open;

Specifically illustrated in SHEET 2:

FIG. 2.1; Flower petals, detached;

FIG. 2.2; Mature leaf;

FIG. 2.3; Receptacle, sepals, reproductive parts;

FIG. 2.4; Bare stem exhibiting thorns.

DETAILED DESCRIPTION OF THE VARIETY

The following is a description of 'POULen009', as observed in its growth in a field nursery in Jackson County, Oreg. Observed plants are 3 years of age, grown on *Rosa multiflora* understock. Color references are made using The Royal Horticultural Society (London, England) Colour Chart, 1995, except where common terms of color are used.

For a comparison, several physical characteristics of the rose variety 'Masdoug1', a non-patented, or applied for rose variety from Guillot and Massard (France) are compared to 'POULen009' in Chart 1.

CHART 1

| | 'POULen009' | 'Masdoug1' |
|---|---|---|
| Height | 100 to 150 cm. | 120 to 150 cm. |
| Peduncle Strength | Somewhat strong | Somewhat weak |
| Number of Flowers per Stem | 5 to 6 | 2 to 3 |

Parents:

*Female seed parent.*—Unnamed plant.

*Male pollen parent.*—'POULsyng'.

FLOWER AND FLOWER BUD

Blooming habit: Recurrent.

Flower bud:

*Bud form.*—Pointed ovoid.

*Bud color.*—As sepals unfold, petals are Yellow-Orange Group 19B with intonations of Yellow Group 10C and longitudinal intonations of Red-Purple Group 58A. The color remains the same at ¼ opening.

*Sepals.*—Upper Surface: Color: Green Group 143B with light intonations of Red-Purple Group 63B. Texture: Smooth and slightly pubescent. Lower Surface: Color: Yellow-Green Group 144A. Anthocyanic pigments the color of Greyed-Red Group 178A. Texture: Smooth with few stipitate glands, occurring on margins of sepals and on foliaceous appendages. Sepal Shape: Sepal apex is cirrhose. Base is flat at union with receptacle. Sepal Margin: Margins have weak foliaceous appendages on three of the five sepals. Size: 25 mm (l)×10 mm (w).

*Receptacle.*—Surface: Smooth and glabrous. Shape: Urn-shaped. Size: 10 mm (h)×9 mm (w). Color: Yellow-Green Group 144B.

*Peduncle.*—Surface: Smooth and glabrous. Length: 40 to 45 mm average length. Color: Yellow-Green Group 144C. Strength: Somewhat strong.

*Borne.*—In small clusters. 5 to 6 flower buds per stem on average.

Flower bloom:

*Fragrance.*—Very strong, sweet perfume like scent.

*Duration.*—The blooms have a duration on the plant of approximately 10 to 14 days. Petals fall cleanly away from plant.

*Size.*—Average flower diameter is 100 mm when open.

*Form.*—General shape is a rosette with outer petals overlapping.

Shape of flower when viewed from the side:

*Upon opening, upper part.*—Flat.

*Upon opening, lower part.*—Flattened convex.

*Open flower, upper part.*—Flat.

*Open flower, lower part.*—Convex.

Petalage: 45 petals under normal conditions with 12 petaloids.

Color:

Upon opening, petals:

*Outermost petals.*—Outer side: Red Group 54D at marginal zone blending with White Group 155B at middle zone. Becoming completely White Group 155B at middle and basal zones. Inner Side: Middle and marginal zones Red Group 54D blending with White Group 155B. Becoming completely White Group 155B at basal zone. Occasional streaking, White Group 155D to red Group 56D from petal base towards margins.

*Innermost petals.*—Outer side: Red Group 54D at marginal zone blending with White Group 155B at middle zone. Becoming completely White Group 155B at middle and basal zones. Inner Side: Middle and marginal zones Red Group 54D blending with White Group 155B. Becoming completely White Group 155B at basal zone.

Upon opening, basal petal spots:

*Outermost petals.*—Outer side: Yellow Group 7C at base of petals. Inner Side: Yellow Group 7C at base of petals.

*Innermost petals.*—Outer side: Yellow Group 7C at base of petals. Inner Side: Yellow Group 7C at base of petals.

After opening, petals:

*Outermost petals.*—Outer side: Red Group 54D at marginal zone blending with White Group 155B at middle zone. Becoming completely White Group 155B at middle and basal zones. Inner Side: Middle and marginal zones Red Group 54D blending with White Group 155B. Becoming completely White Group 155B at basal zone. Occasional streaking, White Group 155D to red Group 56D from petal base towards margins.

*Innermost petals.*—Outer side: Red Group 54D at marginal zone blending with White Group 155B at middle zone. Becoming completely White Group 155B at middle and basal zones. Inner Side: Middle and marginal zones Red Group 54D blending with White Group 155B. Becoming completely White Group 155B at basal zone.

After opening, basal petal spots:

*Outermost petals.*—Outer Side: Yellow Group 7C at base of petals. Inner Side: Yellow Group 7C at base of petals.

*Innermost petals.*—Outer Side: Yellow Group 7C at base of petals. Inner Side: Yellow Group 7C at base of petals.

General tonality: On open flower Red Group 54D with intonations of Red Group 52C. No change in the general tonality at the end of the 10th day.

Petals:

*Petal reflex.*—Outer petals reflex slightly.

*Margin.*—Entire and uniform. Weak undulations of margin.

*Shape.*—Apex is round. Base is acute.

*Size.*—50 mm (l)×48 mm (w).

*Texture.*—Smooth.

*Thickness.*—Average to thin.

*Arrangement.*—Not Formal.

Petaloids:

*Quantity.*—10 to 15.

*Color.*—Upper Surface: Red Group 54D blending with White Group 155B. Lower Surface: Red Group 54D at petal marginal zone. Predominantly White Group 155B throughout.

*Size.*—45 mm (l)×25 mm (w).

Reproductive organs:

*Pistils.*—Length: 3 to 6 mm. Quantity: 70.

*Pollen.*—None observed.

*Anthers.*—Size: 3 mm. Color: Yellow-Orange Group 18C. Quantity: 72 (actual count).

*Filaments.*—Color: Yellow-Orange Group 18A. Length: 8 mm.

*Stigmas.*—Inferior in location to the length of the filaments and height of the anthers. Color: Yellow-Orange 18B.

*Styles.*—Color: Yellow-Orange Group 18B.

*Hips.*—None Observed in the field nursery in Jackson County Oreg.

PLANT

Plant growth: Moderate, upright to bushy. When grown as a budded field grown plant on *Rosa multiflora* understock, the average height of the plant is 100 to 150 cm and the average width is 100 cm.

Stems:

*Color.*—Young wood: Yellow-Green Group 145A to 144B. Older wood: Yellow-Green Group 145A to 144B.

*Surface texture.*—Young wood: Smooth. Older wood: Smooth.

Thorns:

*Incidence.*—8 thorns per 10 cm of stem.

*Size.*—Average length: 6 mm.

*Color.*—Juvenile thorns are Greyed-Red Group 178B to Greyed-Red Group 181A. Mature thorns are Greyed-Yellow Group 161B to Greyed-Orange Group 176A.

*Shape.*—Concave.

Plant foliage:

*Normal number of leaflets on leaves in middle of the stem.*—5 to 7.

*Compound leaf size.*—170 mm (l)×125 mm (w).

*Color.*—Mature Foliage: Upper Leaf Surface: Green Group 138A to Yellow-Green Group 144A. Lower Leaf Surface: Green Group 143C. Juvenile foliage: Upper Leaf Surface: Yellow-Green Group 144A. Lower Leaf Surface: Yellow-Green Group 144B to 144C. Anthocyanin: Location: Margins of juvenile foliage. Color: Greyed-Red Group 178A.

Plant leaves and leaflets:

*Stipules.*—Size: 30 mm in length. Color: Yellow-Green Group 144A. Margins: Finely serrated with above average incidence of stipitate glands.

*Petiole.*—Length: 42 mm. Color: Yellow-Green Group 144C. Underneath: Anthocyanin Greyed-Orange Group 176A.

*Rachis.*—Color: Yellow-Green Group 144C. Underneath: Prickles observed.

*Leaflet.*—Size: 60 to 65 mm (l)×45 to 50 mm (w). Edge: Serrated. Shape: Ovate. Base shape is rounded. Apex is cuspidate. Texture: Smooth. Arrangement: Odd pinnate. Venation: Reticulate. Glossiness: Glossy.

Disease resistance: Above average resistance to mildew, rust, black spot, and Botrytis under normal growing conditions in Jackson County, Oreg.

Cold hardiness: The variety 'POULen009' has been found to be cold tolerant to USDA Cold Hardiness Zone 6.

We claim:

1. A new and distinct variety of rose plant of the hybrid tea rose class, substantially as herein illustrated and described as a distinct and novel rose variety due to its abundant pink, disease resistance, and extended period of bloom.

* * * * *

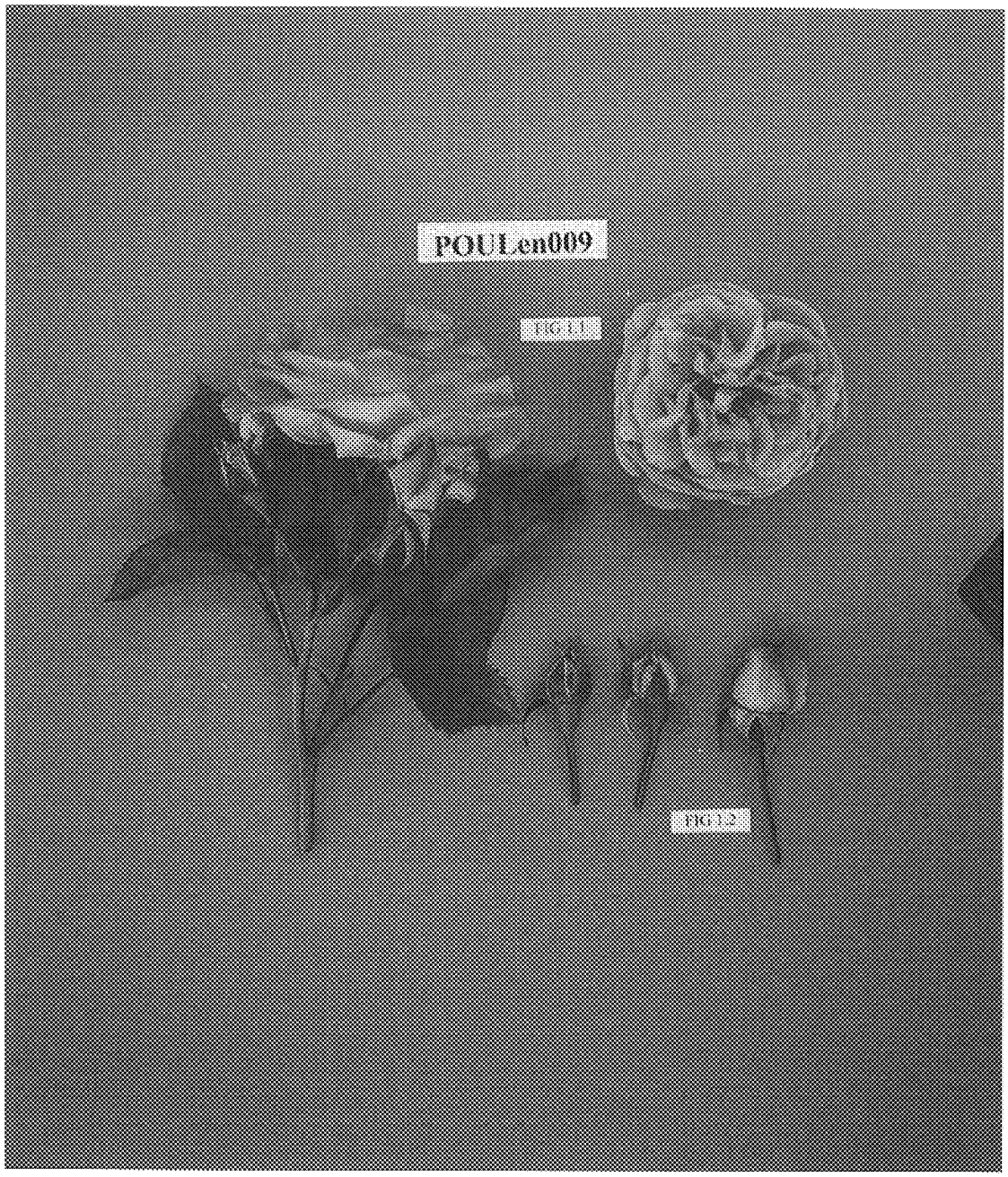
POULen009
FIG.1.1
FIG.1.2

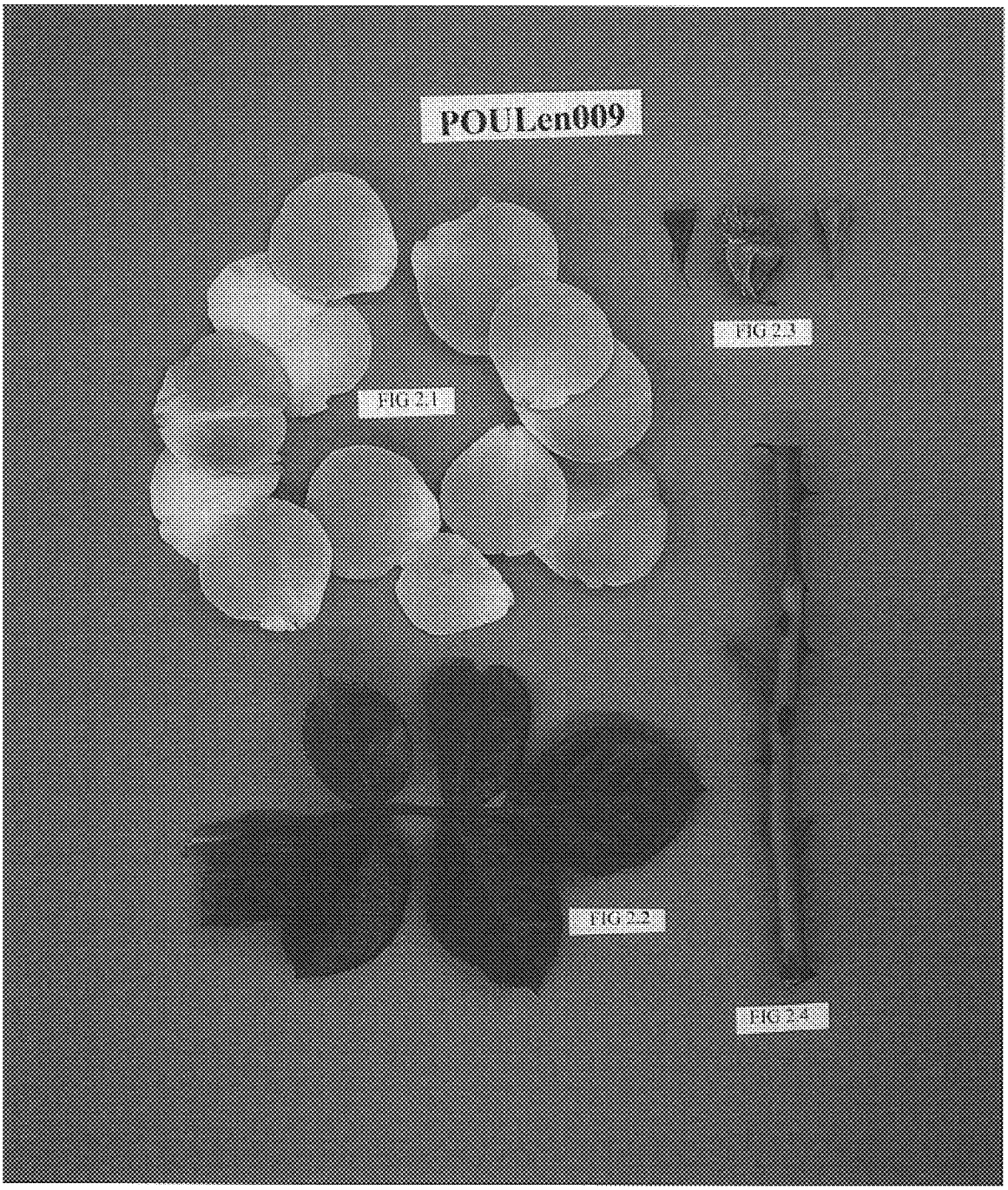
POULen009
FIG 2.1
FIG 2.3
FIG 2.2
FIG 2.4